US010524942B2

(12) United States Patent
Poehlmann et al.

(10) Patent No.: US 10,524,942 B2
(45) Date of Patent: Jan. 7, 2020

(54) IMPLANT, AND SYSTEM FORMED OF A BALLOON CATHETER AND IMPLANT

(71) Applicant: BIOTRONIK AG, Buelach (CH)

(72) Inventors: Stefanie Poehlmann, Rostock (DE); Alexandre Amido, Rostock (DE)

(73) Assignee: BIOTRONIK AG, Beulach (CH)

( * ) Notice: Subject to any disclaimer, the term of this patent is extended or adjusted under 35 U.S.C. 154(b) by 546 days.

(21) Appl. No.: 14/021,716

(22) Filed: Sep. 9, 2013

(65) Prior Publication Data

US 2014/0081371 A1 Mar. 20, 2014

Related U.S. Application Data

(60) Provisional application No. 61/702,767, filed on Sep. 19, 2012.

(51) Int. Cl.
| | |
|---|---|
| *A61F 2/90* | (2013.01) |
| *A61F 2/958* | (2013.01) |
| *A61F 2/915* | (2013.01) |
| *A61F 2/852* | (2013.01) |

(52) U.S. Cl.
CPC ............ *A61F 2/90* (2013.01); *A61F 2/915* (2013.01); *A61F 2/958* (2013.01); *A61F 2/852* (2013.01);
(Continued)

(58) Field of Classification Search
CPC .... A61F 2/86; A61F 2/90; A61F 2/915; A61F 2/958; A61F 2/852; A61F 2002/9155; A61F 2002/91558; A61F 2002/91566; A61F 2002/91575; A61F 2002/91591; A61F 2002/91583; A61F 2002/825; A61F 2002/828; A61F 2002/91508; A61F 2210/0066; A61F 2250/0006; A61F 2250/0007; A61F 2250/0008; A61F 2250/0015; A61F 2250/0029;
(Continued)

(56) References Cited

U.S. PATENT DOCUMENTS

| 5,102,417 A | * | 4/1992 | Palmaz | ............. A61F 2/91 |
| | | | | 604/103.05 |
| 5,807,404 A | * | 9/1998 | Richter | ............. 623/1.16 |

(Continued)

FOREIGN PATENT DOCUMENTS

| DE | 102007012964 A1 | 9/2008 |
| EP | 830853 A1 | 3/1998 |

OTHER PUBLICATIONS

European Search Report for 13181655.5, dated Dec. 2, 2013.

*Primary Examiner* — Katherine H Schwiker
(74) *Attorney, Agent, or Firm* — Wagenknecht IP Law Group PC

(57) ABSTRACT

An implant with an open-worked, hollow cylindrical main structure composed of a multiplicity of crosspieces, wherein the implant adopts a compressed state and an expanded state. So as to achieve a greater level of radial rigidity and an increased collapse pressure in the expanded state compared to conventional implants, wherein the deliverability is not adversely affected at the same time, the density of the crosspieces in the expanded state is greater than the density of the crosspieces in the compressed state, at least in one portion of the implant. The invention further provides a system including a catheter with a balloon and an implant of the type disclosed above.

3 Claims, 10 Drawing Sheets

(52) U.S. Cl.
CPC ............... *A61F 2002/91558* (2013.01); *A61F 2002/91575* (2013.01); *A61F 2002/91583* (2013.01); *A61F 2210/0066* (2013.01); *A61F 2230/0013* (2013.01); *A61F 2250/0006* (2013.01); *A61F 2250/0007* (2013.01); *A61F 2250/0008* (2013.01); *A61F 2250/0015* (2013.01); *A61F 2250/0029* (2013.01); *A61F 2250/0036* (2013.01); *A61F 2250/0048* (2013.01)

(58) Field of Classification Search
CPC .... A61F 2250/0048; A61F 2002/91516; A61F 2/89; A61F 2/91; A61F 2002/91525; A61F 2002/91533; A61F 2002/91541; A61F 2002/826; A61F 2250/0063; A61F 2220/0025; A61F 2220/0033
See application file for complete search history.

(56) References Cited

U.S. PATENT DOCUMENTS

| | | | | |
|---|---|---|---|---|
| 6,190,405 | B1* | 2/2001 | Culombo et al. | 623/1.15 |
| 2002/0111671 | A1* | 8/2002 | Stenzel | A61F 2/91 |
| | | | | 623/1.16 |
| 2002/0188343 | A1* | 12/2002 | Mathis | A61F 2/91 |
| | | | | 623/1.11 |
| 2006/0030932 | A1* | 2/2006 | Kantor et al. | 623/1.16 |
| 2006/0224229 | A1* | 10/2006 | Goto | 623/1.15 |
| 2006/0265048 | A1* | 11/2006 | Cheng | A61F 2/91 |
| | | | | 623/1.15 |
| 2007/0219613 | A1* | 9/2007 | Kao et al. | 623/1.11 |
| 2007/0233232 | A1* | 10/2007 | St. Germain | A61F 2/91 |
| | | | | 623/1.15 |
| 2009/0118810 | A1 | 5/2009 | Klein et al. | |
| 2009/0287241 | A1 | 11/2009 | Berez et al. | |

* cited by examiner

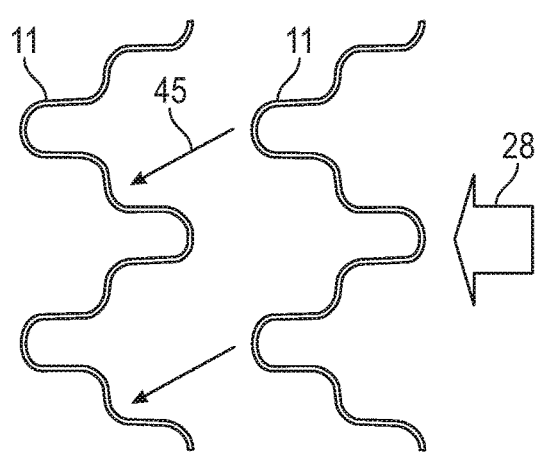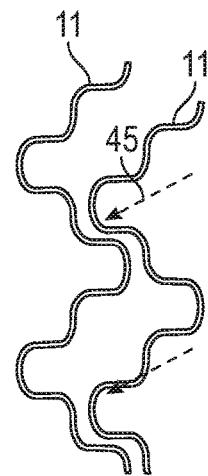
FIG. 21   FIG. 22
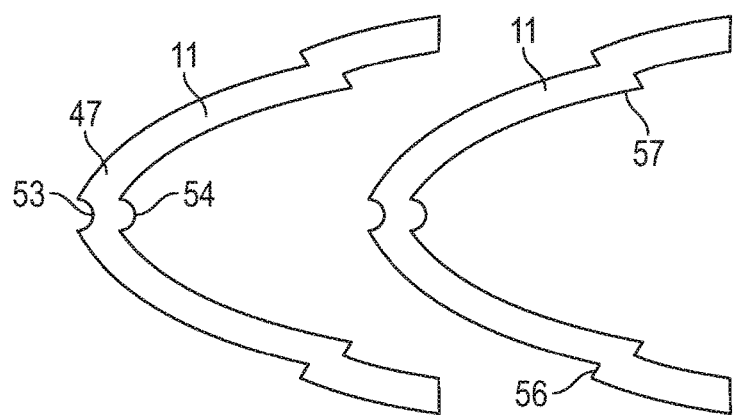
FIG. 23

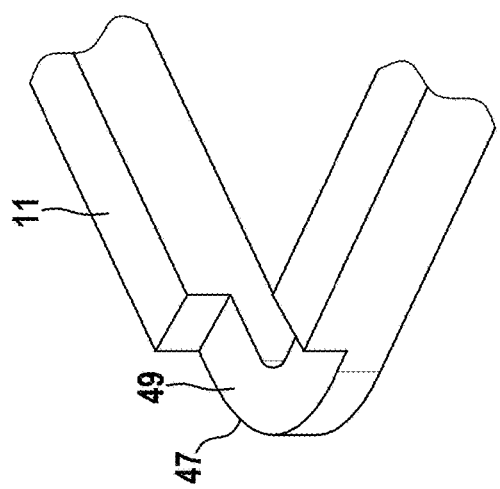
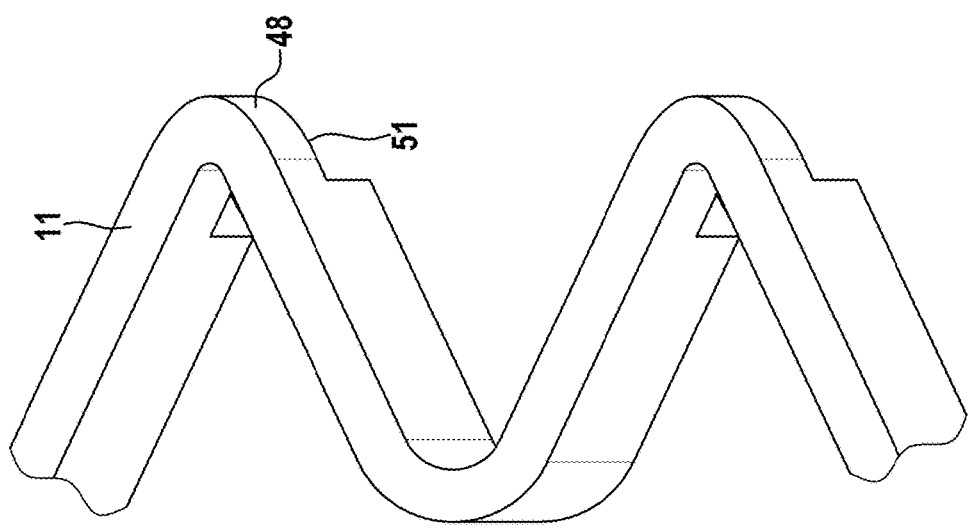
FIG. 24

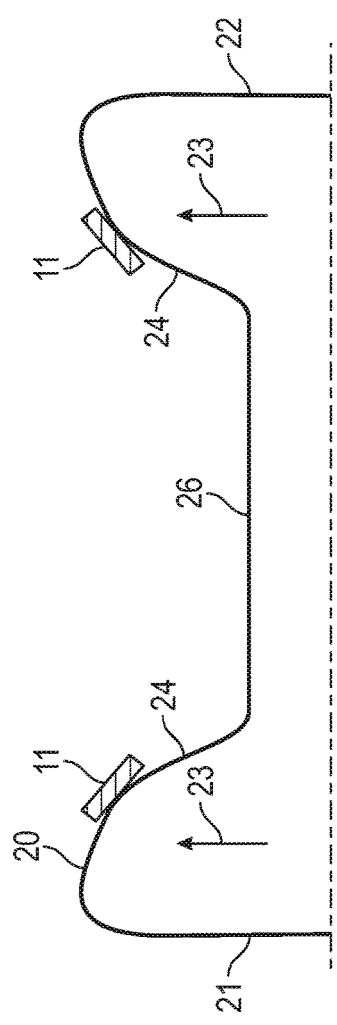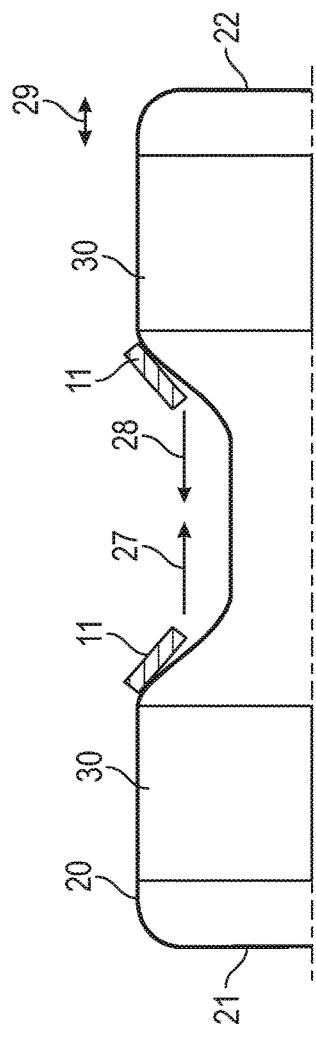

IMPLANT, AND SYSTEM FORMED OF A BALLOON CATHETER AND IMPLANT

CROSS REFERENCE TO RELATED APPLICATIONS

This application claims benefit of priority to U.S. provisional patent application Ser. No. 61/702,767 filed Sep. 19, 2012; the content of which is herein incorporated by reference in its entirety.

TECHNICAL FIELD

The present invention relates to an implant, in particular an intraluminal endoprosthesis, with an open-worked, hollow cylindrical main structure composed of a multiplicity of crosspieces, wherein the implant adopts a compressed state and an expanded state. The invention further relates to a system formed of a balloon catheter and an implant of this type.

BACKGROUND

A wide variety of medical endoprostheses or implants are known from the prior art for a wide range of applications. Within the context of the present invention, implants are to be understood to be endovascular prostheses or other endoprostheses, for example stents (vessel stents (vascular stents, including stents for application in the area of the heart and heart valve stents, for example mitral valve stents and pulmonary valve stents), bile duct stents), endoprostheses for closing patent foramen ovale (PFO), stent grafts for treating aneurysms, endoprostheses for closing an ASD (atrial septal defect), and prostheses in the area of hard and soft tissue.

Nowadays, stents used for treatment of stenoses (vessel constrictions) are used particularly frequently as implants. They have an open-worked hollow cylindrical (tubular) main structure, which is open at both longitudinal ends.

The main structure of conventional stents is often composed of individual meshes, which are formed of a multiplicity of crosspieces (struts), for example of crosspieces forming a zigzagged or meandering structure. An implant of this type is often introduced by means of a catheter into the vessel to be treated and is used to support the vessel over a relatively long period of time (months to years). Due to the use of stents, constricted areas in the vessels can be expanded, thus resulting in a lumen gain.

Stents or other implants normally adopt two states: namely a compressed state with a small diameter and an expanded state with a larger diameter. In the compressed state, the implant can be introduced by means of a catheter into the vessel to be supported and can be positioned at the point to be treated. To this end, the implant is crimped onto the balloon of a catheter for example. The implant is then dilated at the treatment location, for example by means of the balloon of the catheter, and then adopts the expanded state, in which the implant remains in the vessel and supports the vessel, once the catheter with the balloon has been withdrawn again from the body of the patient being treated.

With the use of implants, in particular stents, in hard tissue (for example as vertebral body stents), crosspieces having a very large diameter are currently used so as to achieve the required rigidity, and therefore the tissue structure surrounding the stent is stabilized securely by the stent. Due to the large crosspiece dimensions, implants of this type have a very large diameter on the whole, which is obstructive however in the event of insertion through narrow access paths. The use of stents having a very high level of radial rigidity is also desirable in the case of very severely calcified vessel stenoses. By contrast, implants having a small diameter and a high level of flexibility are required in particular in the case of very severely stenosed vessels or complete closures so as to enable easy placement of the implant without pre-dilation. However, these contrasting properties cannot be implemented by a conventional stent design, or can only be implemented with severe limitations.

Various embodiments of stents have long been known, for example braided wire stents and slotted tube stents, with different cell designs (closed cell design, open cell design or mixtures of both types). Stents with thick crosspieces and closed cell design generally have a high level of radial rigidity, but poor deliverability. By contrast, stents with thin crosspieces and open cell design often have good deliverability, but are less radially rigid.

The term "deliverability" describes the capacity of a stent to be supplied and placed. Deliverability can be measured and described by a number of parameters, for example on the basis of the capacity of the stent to pass through curves or the ability of the stent to move through narrow points. Deliverability is also manifested in the maneuverability of the system.

In the present invention, radial rigidity is understood to be a resistance of an implant (or implant portion) against a force acting in the radial direction, from the outside in with respect to the implant.

Document EP 0 830 853 A1 discloses a stent that is provided, in particular, for application in the area of an ostium. For this application, a relatively high level of radial rigidity is often not necessary over the entire length of the implant, but in particular at the end portion of the stent. The aforementioned document discloses a stent in which for example, in the desired region of the stent, crosspieces are shorter in length compared to other crosspieces, the main structure consists of a material different from that of the remaining part of the main structure, a connecting crosspiece with a U-shape is replaced by a radially more rigid Z-shape or S-shape, or the crosspieces have less material, that is to say are thinner, at least along the other portions. Alternatively, the crosspieces in the desired region may also have more material, that is to say may be thicker. The above solutions are often insufficient in terms of radial rigidity and also have a negative effect on deliverability.

SUMMARY

The object of the present invention therefore lies in creating an implant that has a very high level of radial rigidity and a very high collapse pressure, but of which application is not restricted in terms of deliverability. A further object is to create a system that is formed of a catheter and an implant and has the same advantages.

The above object is achieved by an implant having the features of claim 1.

The implant according to the invention is characterized in particular in that the main structure of the implant is shorter in the expanded state than in the compressed state, and in accordance with the invention the density of the crosspieces in the expanded state is greater than the density of the crosspieces in the compressed state, in particular in at least one portion of the implant.

The stent is compacted by an alternative stent design, described in greater detail further below, in which an axial force during dilation causes portions of the implant to be pushed together (compressed) and thus wedged/meshed and/or locked together. Due to the fact that the crosspieces of the main structure are pushed together, forces that act on the stent externally are better distributed, and therefore a very high level of radial rigidity and a high collapse pressure can be achieved. These properties are only produced, however, with or by the dilation of the implant at the target treatment location in the body of the human or animal. Deliverability, which is important for insertion of the implant and for passage thereof through vessels, is not impaired by this, since the implant still has a flexible structure during these steps, since the meshings and lockings in the main structure are not yet formed at this stage.

A further advantage of the solution according to the invention is that the above-mentioned distribution of the externally acting forces is implemented in particular in specific, predefined portions of the stent, namely in the portions in which the density of the crosspieces is increased by the dilation. The behavior of the stent at the treatment location, which can also be adapted individually, can thus be influenced in a very selective manner.

The density of the crosspieces is established in accordance with the present invention on the basis of the sum of the outer surfaces of all crosspieces in a specific, predefined portion. In this case, the density of the crosspieces in the expanded state is based on the axial length of a specific, predefined portion of the implant in this state. The density of the crosspieces in the compressed state is based on the same portion of the implant, that is to say also on the axial length adopted by this portion in the compressed state. So as to determine the density of the crosspieces in the specific, predefined portion, the sum of the outer surfaces of all crosspieces in this portion is therefore established based on the length of the portion in the respective state, that is to say in the compressed state and in the expanded state respectively. The density of the crosspieces is preferably given in $mm^2/mm$.

In the case of the present innovation, the inventors have found in particular that the ends of the dilation balloon open initially when the implant is dilated. A force in the axial direction, that is to say in the longitudinal direction of the implant, is thus transferred to the implant. This force is used in the main structure of the implant according to the invention to push together at least parts of the structure and to thus cause parts of the structure to mesh or lock together.

In a preferred exemplary embodiment, the increase in density of the implant in the expanded state is 5% to 50% compared to the density of the implant in the compressed state, more preferably 5% to 10%, 10% to 25%, or 25% to 50%, depending on the desired application and the desired radial rigidity, which increases with increasing compaction of the implant.

In the solution according to the invention, all the advantages of a flexible implant with a small profile are present during positioning of the implant in the compressed state, since in this state the structures are not yet locked/meshed together. During expansion, the advantages of a rigid implant having thick crosspieces and closed cell design are then activated and are effective.

In a particularly preferred exemplary embodiment, with a main structure that consists of a multiplicity of circumferential portions, which each have a zigzagged, waved, sinusoidal, meandering or similar crosspiece structure extending in the circumferential direction, wherein the circumferential portions may also be formed helically, and that is composed of a multiplicity of connecting crosspieces, which extend substantially in the axial direction and link together the circumferential portions, the connecting crosspieces and/or the crosspiece structures of the circumferential portions have means so that at least part of the crosspiece structure of at least a first circumferential portion is meshed and/or locked in the expanded state with at least part of the crosspiece structure of the adjacent circumferential portion. In the compressed state, there is no meshing and/or locking of the crosspiece structures of adjacent circumferential portions, and the meshing and/or locking is only implemented by the dilation, in particular by means of the above-explained axial forces applied to the implant. As a result of the meshing and/or locking, an at least partial overlap of the crosspiece structures of adjacent circumferential portions can be achieved.

The structure formed of a multiplicity of zigzagged, waved, sinusoidal, meandering or similar crosspieces, which extends in the circumferential direction of the implant and forms a circumferential portion, will also be referred to hereinafter as a basic meander. Such a basic meander specifically also comprises, besides an annular structure, a helical structure formed of crosspieces. In this case, a circumferential portion is formed by a helical structure, which initially passes around the implant exactly once, that is to say forms an angle of 360°. Such a basic meander is not restricted to a meandering structure. Rather, it may also have any other form extending in the circumferential direction, for example a waved, zigzagged or sinusoidal form, or the like.

With a design of this type of an implant according to the invention, the properties of the implant can set particularly easily and possibly over portions, for example in accordance with the structure of the vessel to be treated. In particular, the form and flexibility of the connecting crosspieces can control whether the basic meanders are to mesh or lock and possibly overlap during dilation. The design of the basic meanders influences, in particular, the type of locking or meshing between the adjacent circumferential portions.

It is particularly preferable if the connecting crosspieces are flexible, such that they assist the meshing or locking of crosspieces of adjacent basic meanders during dilation, preferably by means of a balloon.

In this case, the connecting crosspieces can be designed in such a way that at least some of them are rotatable about an axis extending in the radial direction when subject to a force acting substantially in the axial direction. The axis of rotation may be arranged, in particular, in the region of the transition from the respective connecting crosspiece to the adjacent crosspiece of the basic meander. It is also advantageous for rotation of the connecting crosspiece if said crosspiece is more rigid over the majority of its length than the transition regions to the adjacent basic meanders arranged at the ends of said connecting crosspiece.

Alternatively or in addition, at least some of the connecting crosspieces can be compressed under a force acting substantially in the axial direction. In this embodiment, the respective connecting crosspiece is deformed in such a way that its effective length is shortened. For this variant, the shortening of the distance between the adjacent basic meanders is advantageous if the respective connecting crosspiece is more flexible over the majority of its length than in the transition regions arranged at the ends and in which the connecting crosspiece is connected to the adjacent basic meanders.

In the latter case, the connecting crosspieces may have a tapering in the apex points for example. In the former variant, in which the connecting crosspieces rotate, a tapering can be provided at the ends of the connecting crosspieces for example. In particular, S-shaped connecting crosspieces, U-shaped connecting crosspieces and Z-shaped connecting crosspieces, the latter in particular with a curved central portion, are advantageous for compression of the connecting crosspieces.

With the above-described advantages, the object is also achieved by a system comprising a catheter with a balloon and an above-described implant according to claim 7, wherein the implant is arranged on the balloon in the compressed state.

It is further advantageous if the balloon of the catheter is longer than the implant and protrudes beyond the distal and/or proximal end of the implant by at least 1% of the length of the implant or by 0.5 mm, depending on which length is greater. Due to the overhang at the balloon shoulders, the force acting in the axial direction on the implant, which pushes the implant together, can be intensified during dilation. It is important that the balloon shoulders can expand freely, so as to compress the stent during dilation.

The implant according to the invention will be explained hereinafter in exemplary embodiments on the basis of the figures. All described features and/or those illustrated in the figures form part of the subject of the invention, irrespective of the summary thereof in the claims and the back-references of the claims.

DESCRIPTION OF THE DRAWINGS

Unless indicated otherwise, the figures show schematic views from above as follows.

DETAILED DESCRIPTION

Figure 1:
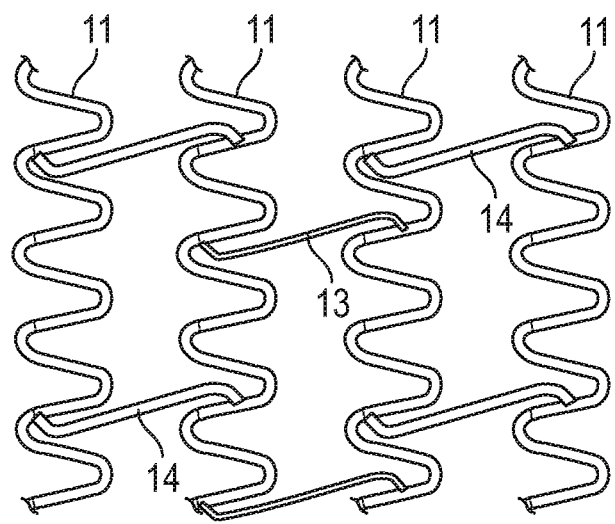
FIG. 1 a detail of a two-dimensional development of a first exemplary embodiment of an implant according to the invention in the compressed state, FIG. 2 the detail of the development of the exemplary embodiment according to FIG. 1 in a first expanded state, FIG. 3 the detail of the development of the exemplary embodiment according to FIG. 1 in a second expanded state, FIG. 4 a connecting crosspiece, which is connected at both its ends to a respective crosspiece of adjacent basic meanders, FIGS. 5 to 7 variants of connecting crosspieces that are suitable for rotation of the connecting crosspiece during dilation FIGS. 8 to 10 variants of connecting crosspieces that are suitable for compression/shortening of the connecting crosspiece during dilation, FIG. 11 a detail of a two-dimensional development of a second exemplary embodiment of an implant according to the invention in the compressed state, FIG. 12 the detail of the development of the exemplary embodiment according to FIG. 11 in the expanded state, FIG. 13 a detail of a two-dimensional development of a third exemplary embodiment of an implant according to the invention in the compressed state, FIG. 14 the detail of the development of the exemplary embodiment according to FIG. 13 in the expanded state, FIG. 15 a detail of a two-dimensional development of a fourth exemplary embodiment of an implant according to the invention in the compressed state, without the respective connecting crosspieces, FIG. 16 the detail of the development of the exemplary embodiment according to FIG. 15 in the expanded state, FIG. 17 a detail of a two-dimensional development of a fifth exemplary embodiment of an implant according to the invention in the compressed state, without the respective connecting crosspieces, FIG. 18 the detail of the development of the exemplary embodiment according to FIG. 17 in the expanded state, FIG. 19 a detail of a two-dimensional development of a sixth exemplary embodiment of an implant according to the invention in the compressed state, without the respective connecting crosspieces, FIG. 20 the detail of the development of the exemplary embodiment according to FIG. 19 in the expanded state, FIG. 21 a detail of a two-dimensional development of a seventh exemplary embodiment of an implant according to the invention in the compressed state, without the respective connecting crosspieces, FIG. 22 the detail of the development of the exemplary embodiment according to FIG. 20 in the expanded state, FIG. 23 crosspieces of adjacent basic meanders of an eighth exemplary embodiment of an implant according to the invention in the compressed state, without the respective connecting crosspieces, FIG. 24 a perspective view, from the side without the respective connecting crosspieces, of crosspieces of adjacent basic meanders of a ninth exemplary embodiment of an implant according to the invention in the compressed state, FIG. 25 a cross section through half of a balloon of a catheter in a first exemplary embodiment of a system according to the invention during dilation, FIG. 26 a cross section through half of a balloon of a catheter in a second exemplary embodiment of a system according to the invention during dilation, and FIG. 27 a detail of a two-dimensional development of a further exemplary embodiment of an implant according to the invention.

The first exemplary embodiment is based on a stent, for example an ostium stent, which is hollow cylindrical and is composed of portions (basic meanders) 11 extending in the circumferential direction and having waved or sinusoidal crosspieces and S-shaped connecting crosspieces 13, 14. Each basic meander 11 is connected to the next basic meander 11 either via flexible connecting crosspieces 13 or via comparatively rigid, S-shaped connecting crosspieces 14. The rigid connecting crosspieces 14 have a larger diameter compared to the flexible connecting crosspieces 13 and are therefore stiffer/more rigid. The connecting crosspieces 13, 14 extend substantially in the direction of the longitudinal axis (hereinafter: axial direction) of the stent.

If the stent is then dilated by means of a balloon 20 once the stent has been inserted for treatment of a human or animal at the desired point, for example in an ostium, as shown in FIGS. 25 and 26, the stent thus opens initially at its distal end 21 and its proximal end 22. As is illustrated in FIGS. 25 and 26 merely by two basic meanders 11, arranged at the proximal and distal end of the stent respectively, the stent sits in the central part 26 of the balloon 20 and is crimped thereon for example. The areas 24, 25 at the flanks of the balloon 20 between the already expanded tube ends 21, 22 and the as yet unexpanded central part 26 produce a force component in the axial direction during expansion (arrow 23) of the balloon by inflation, said force component acting on the stent during dilation and thus pushing together the basic meanders 11 in the axial direction. This axial force is produced since the balloon 22 always unfolds starting from its ends 21, 22. The force impressed by the balloon 20 onto the stent in the axial direction and the axial direction itself are illustrated in FIG. 26 by the arrows 27, 28 and in FIG. 2 by the arrow 28. The magnitude of the force acting on the stent in the axial direction can be controlled by the length of the overhang 29 of the balloon 20, that is to say by the length over which the balloon 20 protrudes beyond the stent at the ends. The frictional properties of the balloon 20 against the stent further determine how strongly the balloon 20 responds to this force, that is to say the strength of the compression of the balloon. The area denoted by reference sign 30 in FIGS. 25 and 26 represents the sliding area, in which the stent ends on the balloon have been slid over the balloon 20 in the longitudinal direction. The compression of the stent and therefore the increase in density is caused by this sliding of the stent and balloon 20 relative to one another. The size of the sliding region is determined by the force in the axial direction, the frictional properties of the stent and balloon, and the flexibility of the stent. After dilation, the stent is compressed to such an extent that the stent is no longer arranged on the sliding region 30, but only inside thereof.

Figure 2:
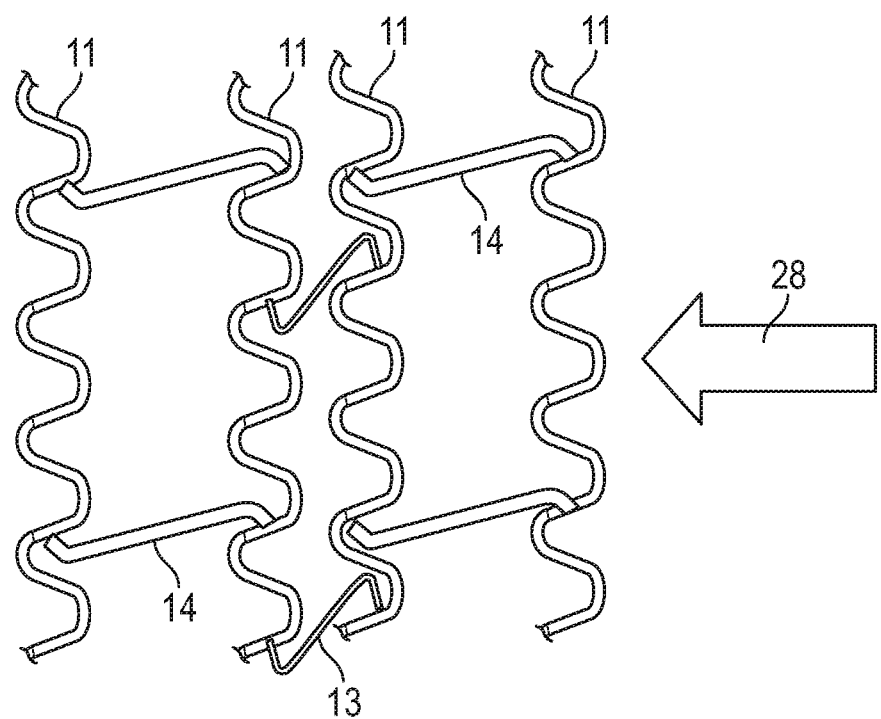

As illustrated in FIG. 2, the force in the axial direction in particular causes a compression/shortening of the flexible crosspieces 13. These are curved severely by the axial force (arrow 28), in particular in the region of the apex points of the S-shape (where the radii of curvature are reduced), in such a way that their effective length in the axial direction is reduced. This results in the basic meanders 11 connected by the flexible connecting crosspieces 13, that is to say the two central basic meanders 11 shown in FIGS. 1 and 2, being moved toward one another and meshed/wedged together. The collapse pressure and the radial rigidity of the stent are thus increased many times over.

Figure 3:
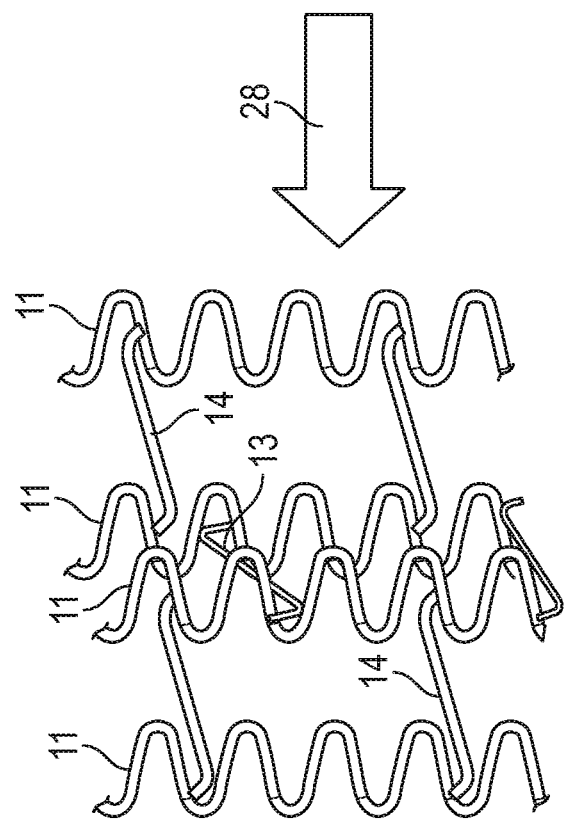

FIG. 3 shows the first exemplary embodiment in the expanded state with more flexible connecting crosspieces 13 or a greater force applied in the axial direction. The connecting crosspieces have been deformed by the force in the axial direction to such an extent that the basic meanders 11 adjacent to the flexible connecting crosspieces 13 mesh and overlap and thus present an even greater shortening. The stent shown in FIG. 3 thus has a significantly increased radial rigidity and a significantly increased collapse pressure compared to the stent illustrated in FIG. 2 (with identical materials). The adjacent central basic meanders in FIG. 3 overlap, in particular in the region of the apex of the sinusoidal structure.

The rigid connecting crosspieces 12 do not deform during the dilation process, and therefore the distances between the basic meanders 11 that are interconnected by these rigid connecting crosspieces 14 do not change.

Figure 4:
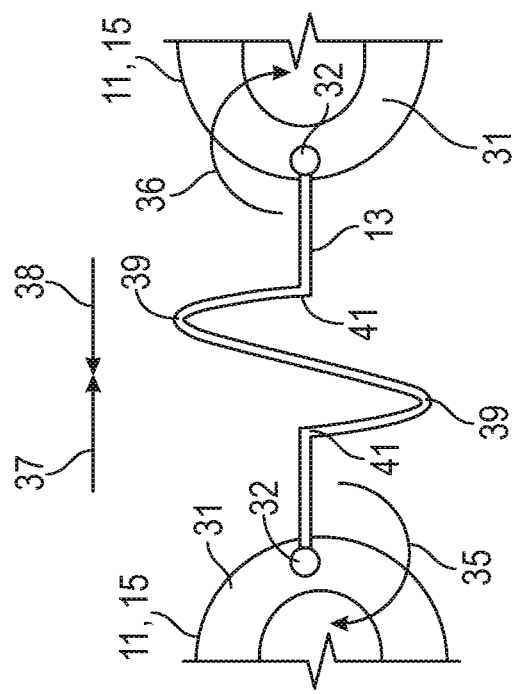

The different possibilities for shortening flexible connecting crosspieces 13 are explained in principle with reference to FIG. 4. It has already been mentioned above that a shortening of the distances between adjacent basic meanders 11 in the axial direction can be achieved in principle by rotating the corresponding connecting crosspieces, during dilation, about an axis extending in the radial direction or by deforming the connecting crosspieces, during dilation, between their two respective ends. In practice, both possibilities are often implemented, more or less at the same time.

To rotate the connecting crosspiece 13, the regions 31 at the ends of the connecting crosspiece 13, in which the connecting crosspiece 13 is connected to a crosspiece 15 of the adjacent basic meander 11, are flexible in a preferred exemplary embodiment. Due to this flexibility, the connecting crosspiece 13 can rotate about an axis 32 arranged in each region 31, wherein the rotation runs in the same direction at both ends. The rotational movement is illustrated by means of the circular-arc-shaped arrows 35, 36 in FIG. 4.

Alternatively or in addition to the rotation, the connecting crosspiece 13 can also be shortened by deformation in its effective length in the axial direction as a result of the force applied in the axial direction (see arrows 37, 38). In particular, the deformation affects the apex points 39 and the end regions 41 of the S-shape of the connecting crosspiece 13. So as to assist the deformation at these points, the connecting crosspiece 13 can be made particularly flexible at the apex points 39 and end regions 41, for example by a reduced crosspiece diameter in these regions. When the force in the axial direction is effective (arrows 37, 38), the connecting crosspiece 13 deforms in such a way that the radius of curvature at the apex points 39 and in the end regions 41 is reduced.

Figure 8:
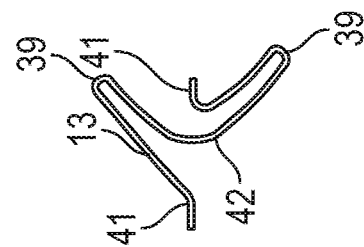
Figure 9:
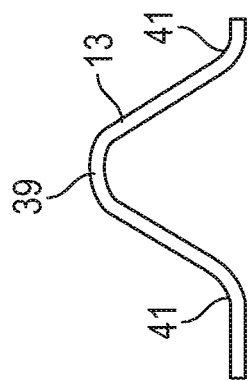
Figure 10:
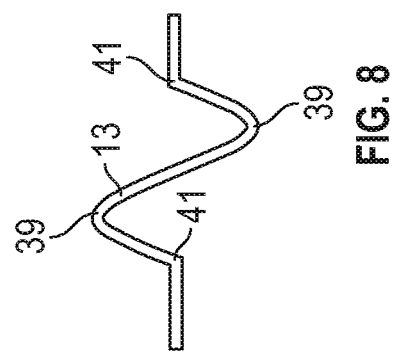

FIGS. 8 to 10 show some examples for the design of connecting crosspieces 13, which deform easily when subject to a force in the axial direction so that the effective length of the connecting crosspiece 13, which determines the distance between the adjacent basic meanders 11, is shortened. FIG. 8 shows a substantially sinusoidal connecting crosspiece 13, which deforms in particular at its apexes 39 and at the end regions 41 of the sinusoidal shape. FIG. 9 illustrates a U-shaped connecting crosspiece 13, which likewise can be deformed at an apex 39 or at the end regions 41 of the "U". FIG. 10 shows a further connecting crosspiece 13, which has a Z-shape, wherein the central part 42 of the Z is additionally curved. In this case, too, the deformation is preferably implemented in the regions of the apexes 39, the end regions of the Z-shape 41 and in the region of the central part 42.

Figure 5:
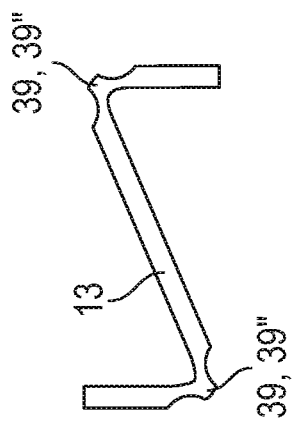
Figure 6:
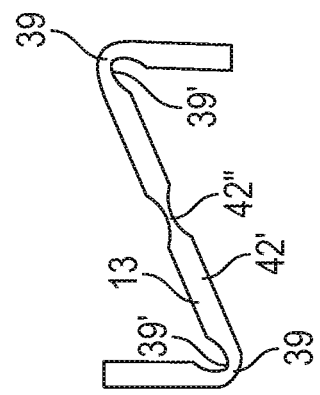
Figure 7:
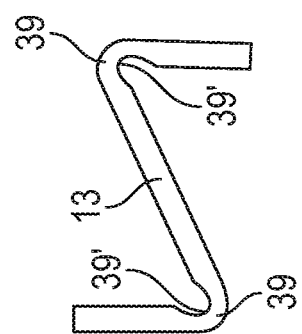

The connecting crosspieces shown in FIGS. 5 to 7 can also be deformed easily when subject to a force in the axial direction and produce a shortening of the effective length of the respective connecting crosspiece 13, similarly to the connecting crosspieces shown in FIGS. 8 to 10. FIGS. 5 to 7 contain sinusoidal connecting crosspieces 13, which deform in particular at the apexes 39, since they have a reduced thickness at these points. The connecting crosspiece 13 shown in FIG. 5 has a thickness reduction at the inner face 39' of each apex 39, whereas in the connecting crosspiece 13 illustrated in FIG. 7 the thickness reduction is achieved by two corresponding recesses in the outer face 39" of each respective apex 39. The connecting crosspiece 13 sketched in FIG. 6 has a thickness reduction at the inner face 39' of each apex 39, similarly to the connecting crosspiece shown in FIG. 5. In addition, a further region 42" in the central crosspiece region 42' between the two apexes 39 is provided with a thickness reduction along a large part of the circumference in the region 42". The thickness reduction causes the connecting crosspiece 13 to buckle in the region 42", thus producing a further shortening of the effective length, similarly to the Z-shape shown in FIG. 10.

Figure 11:
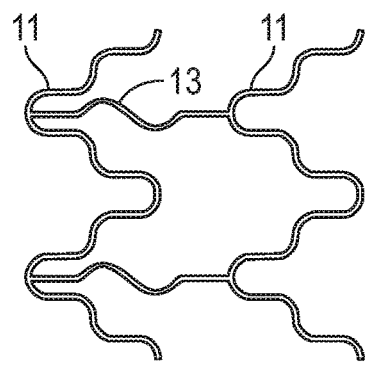
Figure 12:
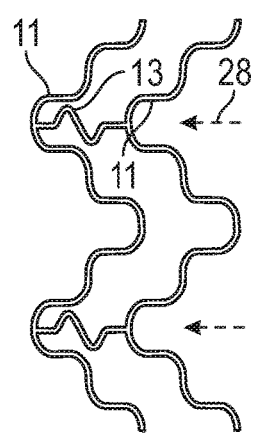

In the second exemplary embodiment of an implant according to the invention in the form of a stent, as illustrated in FIGS. 11 and 12, the basic meanders 11, which can be characterized as a sinusoidal shape with steps, are connected by a sinusoidal connecting crosspiece 13. During dilation, the force applied in the axial direction by the balloon (see arrow 28) leads to a shortening of these connecting crosspieces 13 due to a deformation in particular in the region of the apexes 39 and the end regions 41, similarly to the explanations given for FIG. 8. The shortening of the distance between the basic meanders 11 leads to a meshing of the adjacent basic meanders, particularly if the structures are arranged so as to fit into one another once said distance has been shortened.

Figure 13:
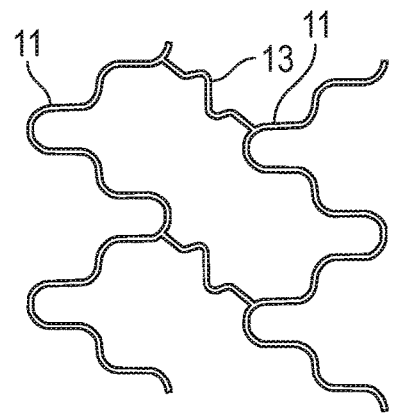
Figure 14:
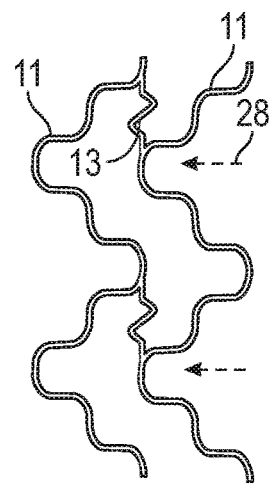

In the third exemplary embodiment illustrated with reference to FIGS. 13 and 14, the connecting crosspieces 13 between the basic meanders 11 are arranged inclined to the longitudinal direction of the stent in the compressed state and are sinusoidal in shape, similarly to the second exemplary embodiment. Each connecting crosspiece 13 is designed so as to be flexible, in particular in the regions 31 connecting to the basic meanders 11, so that the axial force (see arrow 28) produced during balloon dilation leads to a rotation of the connecting crosspieces 13 about axes extending in the radial direction, similarly to the rotation illustrated with reference to FIG. 4. In addition, the connecting crosspieces 13 deform similarly to the second exemplary embodiment and thus further shorten the distance between the adjacent circumferential portions 11. Similarly to the second exemplary embodiment, the shortening, thus produced, of the distance between the basic meanders 11 is implemented by a meshing of the adjacent basic meanders 11, which, in the expanded state, are arranged similarly to the second exemplary embodiment so that they fit into one another.

The movement of the adjacent basic meanders 11 relative to one another during dilation can thus also be controlled by the design of the connecting crosspieces. This also leads to different meshing variants. Different movements and meshing variants will be described with reference to the following exemplary embodiments.

Figure 15:
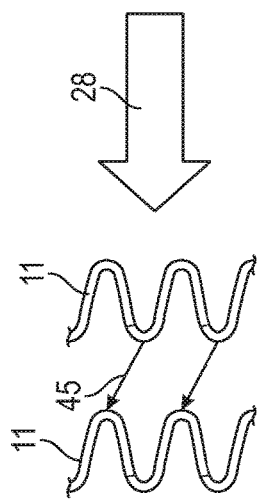
Figure 16:
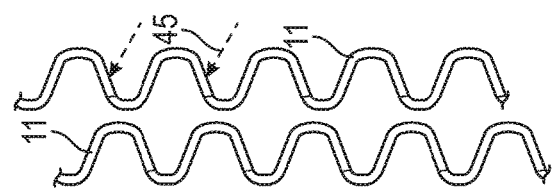

Similarly to the second exemplary embodiment, the fourth exemplary embodiment illustrated in FIGS. 15 and 16 shows a movement of the adjacent circumferential portions merely in the axial direction (see arrow 43) during dilation as a result of the applied force in the axial direction (arrow 28). Similarly to the second exemplary embodiment, the basic meanders 11 are arranged in such a way at the end of the dilation process that the sinusoidal structures of the basic meanders "fit" into one another and thus mesh together. In other words, the regions of the adjacent basic meanders 11 protruding in the distal direction and the respective regions of the adjacent basic meanders 11 protruding in the proximal direction lie opposite one another.

Figure 17:
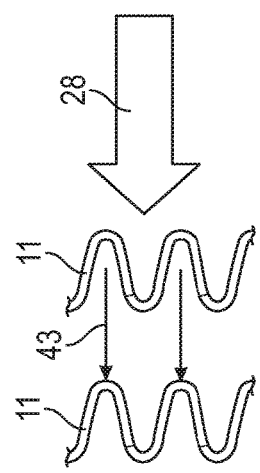
Figure 18:
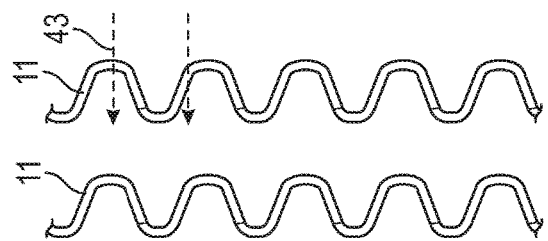

In the fifth exemplary embodiment illustrated in FIGS. 17 and 18, the adjacent circumferential portions 11 move inclined to the axial direction (see arrow 45) during balloon dilation, similarly to the third exemplary embodiment. In addition, the adjacent circumferential portions 11 are arranged in such a way in the expanded state that the sinusoidal structures of the basic meanders do not "fit" together. In other words, in the expanded state, a region of the basic meander 11 protruding in the proximal direction lies opposite a region of the adjacent basic meander 11 protruding in the distal direction, and vice versa. Such an arrangement is particularly advantageous if the structures are to become wedged with one another, for example as a result of direct contact or overlap in the expanded state (see also the explanations given below with reference to FIG. 24).

Figure 19:
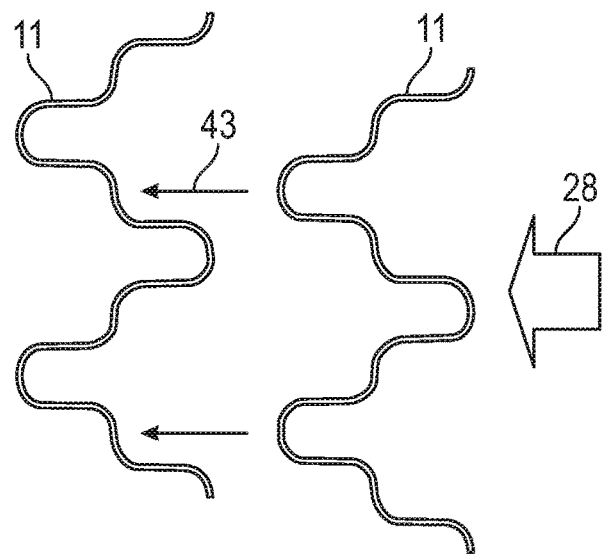
Figure 20:
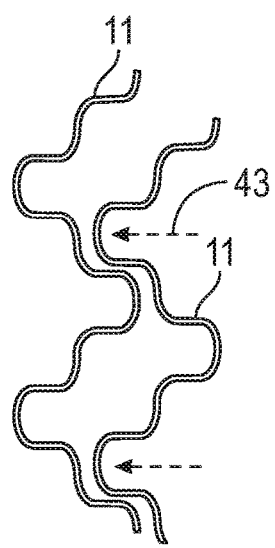

Similarly to the second and fourth exemplary embodiments, the sixth exemplary embodiment illustrated in FIGS. 19 and 20 shows a displacement of the adjacent basic meanders 11, merely in the radial direction of the stent during balloon dilation. By contrast, the displacement in the seventh exemplary embodiment, which is illustrated in FIGS. 21 and 22, is implemented in a direction inclined to the axial direction, similarly to the third and fifth exemplary embodiments. In the exemplary embodiments according to FIGS. 19 and 20 as well as FIGS. 21 and 22, the adjacent circumferential portions mesh together since a central portion having a lateral protrusion (in the circumferential direction) of a first basic meander 11 becomes engaged, in a sub-region of the meander shape, with a portion of an adjacent second basic meander protruding in the distal direction, Two variants of structures that can mesh together particularly effectively due to their shape are explained with reference to the crosspiece portions, shown in FIG. 23, of two adjacent basic meanders 11. In the region of the apex 47, the crosspiece portions each have a semi-cylindrical or semi-spherical recess 53, and on the opposite side they each have a substantially semi-cylindrical or semi-spherical protrusion 54, in the axial direction in each case. At the end of the dilation process and in the expanded state, the protrusion 54 of the crosspiece portion in the apex region 47 is placed in, or close to, the opposed recess 53 in the crosspiece portion of the adjacent basic meander 11, so that these structures form a positive fit. Effective meshing is thus produced. The same also applies to the steps 56, 57 which are provided laterally on the crosspieces, transverse to the radial direction, and which each form a positive element on one side of the crosspiece and a corresponding negative element on the other side of the crosspiece. In the event of displacement during balloon dilation, these steps 56, 57 also become engaged or are placed in the vicinity of one another.

If the basic meanders 11 are overlapped, a design of the crosspieces as shown in FIG. 24 can be implemented in particular. In this case the regions 47, 48 provided for the overlap (in this case: apex regions, although further regions are also conceivable) have recesses 49, 51 in the respective upper face or the respective lower face, which are arranged such that mutually opposed regions complement one another when they overlap in the expanded state. For example, recesses 49 are provided on the outer face of the stent at all apexes 47 protruding in the distal direction, and recesses 51 are provided on the inner face of the stent at all apexes 48 protruding in the proximal direction. This possibility is a particularly effective and simple possibility for providing a meshing between the adjacent basic meanders 11.

The exemplary embodiments, described in greater detail above, of an implant according to the invention are characterized by a very high level of radial rigidity and a high collapse pressure, which are only initiated however by the dilation of the implant and therefore only occur in the expanded state. All the advantages of a flexible implant with a small profile can therefore be utilized when positioning and guiding the stent in the vessel system of the human or animal to be treated, in particular good deliverability, low forces for positioning, good capacity to pass through curves, small entry profile into the stenosis, good possibilities for "direct stenting" (without pre-dilation, which is otherwise necessary), and good handling and "feel" for the doctor when stenting. Due to the change of state during dilation, the advantages of a rigid implant can be combined with those of a flexible implant. Furthermore, the degree of stiffening can be controlled by the design of the implant, and the location of the stiffening can be set selectively for the respective application by the implant according to the invention, in particular by the arrangement and embodiment of the connecting crosspieces 13. For example, ostium stents may require reinforcement merely at one end of the stent. In addition, the degree of stiffening can also be adapted to the various applications (implants for specific stenosis types, stents in hard tissue, for example vertebral body stents). Furthermore, the degree of the stiffening can be controlled by the embodiment of the balloon. In particular, the length of the overhang 29 of the balloon 20 beyond the applied, preferably crimped-on, stent determines the magnitude of the forces impressed onto the stent in the axial direction.

Example of Use

Figure 27:
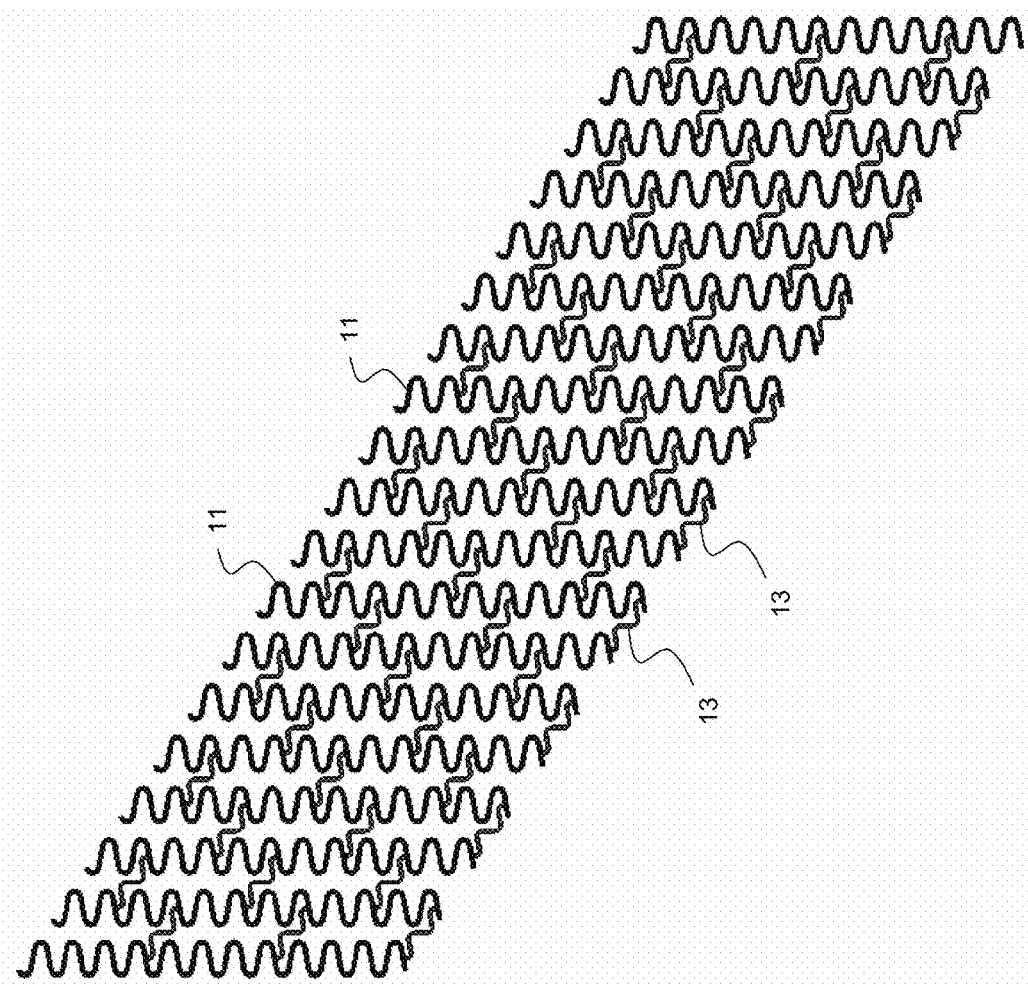

Test samples are Cobalt Chromium Coronary Stents with a nominal diameter of 3.0 mm and a nominal length of 14.05 mm. The design of the test samples is shown in FIG. 27 and consists of a waved basic meander 11 with sinusoidal connecting crosspieces 13.

Previous to testing, the test samples are manually crimped using a manual crimp tool set for 0.9 mm diameter (known in the art) on a balloon system with a nominal diameter of 3.0 mm and a nominal length of 15.0 mm. These balloon systems are known in the art. After crimping the samples are separated in two groups of respectively 5 samples:

Group 1 (The not compressed group): The samples are not compressed and directly expanded in artery models with a diameter of 3.0 mm. The samples are tested without additional change.

Group 2 (The compressed group, according to the invention): After a first expansion to nominal pressure (9 atm) without artery models, the samples are axially compressed using a tensile testing machine with axial compression testing tools. Additionally, after the axial compression, the samples are postdilated in an artery model with a diameter of 3.0 mm.

The stent expansion in artery models with a diameter of 3.0 mm is conducted in order to ensure a homogeneous expansion diameter among all test samples.

The following parameters are extracted from the data analysis:

The radial rigidity (i.e. the change in diameter as a function of uniformly applied external radial pressure) is defined as the slope of pressure versus outer diameter for diameter reductions from 3% to 7% from initial diameter.

The radial strength (i.e. the pressure at which a stent experiences irrecoverable deformation) is defined as the maximum measured radial force for diameters comprised between the initial diameter and 15% diameter reduction from initial diameter.

Further group 1 and 2 are compared regarding radial strength and radial rigidity using Student's t-test.

The testing of the different parameters is conducted according to testing instructions well known in the art.

The results are summarized in Table 1 below:

Stents from the compressed group (group 2) display a mean expanded length of 7.8 mm resulting in a theoretic foreshortening of 44.7% while the not compressed group (group 1) have a mean length of 12.2 mm and a foreshortening of 13.4%.

The radial rigidity as well as the radial strength are both higher for group 2 as for group 1 with respectively 17.1 atm/mm and 4.4 N/mm compared to 10.6 atm/mm and 2.8 N/mm.

Additionally the differences between both groups regarding radial rigidity and radial strength are statistically significant with Student's t-test P-value<0.05.

Stents according to the present invention shorten during balloon expansion and have higher radial rigidity and radial strength than stents which do not shorten.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

11 basic meander (circumferential portion)
13, 14 connecting crosspiece
15 crosspiece of the basic meander 11
20 balloon
21 distal end of the balloon 20
22 proximal end of the balloon 20
23 arrow
24, 25 portion of the balloon 20
26 central part
27, 28 arrow
29 overhang
30 sliding region
31 region of the connection between connecting crosspiece 13 and basic meander 11
32 axis of rotation
35, 36 circular-arc-shaped arrow
37, 38 arrow
39 apex
39' inner face of the apex 39

TABLE 1

| | N° | Nominal length [mm] | Length [mm] | Diameter* [mm] | radial rigidity [atm/mm] | Foreshortening [%] | radial strength [N/mm] |
|---|---|---|---|---|---|---|---|
| Group 2 | 1 | 14.05 | 9.46 | 3.14 | 17.045 | 32.7 | 3.604 |
| | 2 | 14.05 | 8.50 | 3.13 | 16.263 | 39.5 | 3.800 |
| | 3 | 14.05 | 5.11 | 3.10 | 19.199 | 63.6 | 6.104 |
| | 4 | 14.05 | 8.17 | 3.13 | 14.611 | 41.9 | 4.215 |
| | 5 | 14.05 | 7.63 | 3.13 | 18.434 | 45.7 | 4.459 |
| Mean value | | | 7.77 | 3.13 | 17.11 | 44.67 | 4.44 |
| Standard Deviation | | | 1.63 | 0.02 | 1.81 | 11.61 | 0.99 |
| Group 1 | 6 | 14.05 | 11.90 | 3.12 | 9.651 | 15.3 | 2.794 |
| | 7 | 14.05 | 12.36 | 3.13 | 10.890 | 12.0 | 2.708 |
| | 8 | 14.05 | 12.34 | 3.16 | 10.972 | 12.2 | 2.755 |
| | 9 | 14.05 | 12.48 | 3.12 | 9.762 | 11.2 | 2.847 |
| | 10 | 14.05 | 11.77 | 3.14 | 11.930 | 16.2 | 2.957 |
| Mean value | | | 12.17 | 3.13 | 10.64 | 13.38 | 2.81 |
| Standard Deviation | | | 0.31 | 0.02 | 0.95 | 2.23 | 0.10 |
| Student's t-test group 2/group 1 P-value | | | | | 0 | | 0.022 |

*after dilatation

39" outer face of the apex 39
41 end region of the respective shape
42 central part of the Z-shape
42' central region of the connecting crosspiece
42" region with thickness reduction
43, 45 arrow
47, 48 apex
49, 51 recess
53 recess
54 protrusion
56, 57 step

What is claimed is:

1. An implant with an open-worked, hollow cylindrical main structure consisting essentially of circumferential meandering structures joined by a multiplicity of crosspieces, wherein the implant adopts a compressed state and an expanded state, characterized in that radial expansion of the main structure increases compression of the crosspieces to increase density of the crosspieces in at least in one portion of the implant that is straight in a longitudinal direction of the implant when expanded, and further characterized in that the meandering structures and adjacent meandering structures comprise complementary structures that fit into one another to directly mesh the meandering structures with the adjacent meandering structures in the implant's expanded state and further wherein the meandering structures and adjacent meandering structures are free from direct contact with one another in the implant's compressed state;

wherein the meandering structures and adjacent meandering structures are meshed by a lateral protrusion of the meandering structure engaged with a portion of a lateral protrusion of the adjacent meandering structure;

wherein the protrusions protrude in a same direction.

2. An implant with an open-worked, hollow cylindrical main structure consisting essentially of circumferential meandering structures joined by a multiplicity of crosspieces, wherein the implant adopts a compressed state and an expanded state, characterized in that radial expansion of the main structure increases compression of the crosspieces to increase density of the crosspieces in at least in one portion of the implant that is straight in a longitudinal direction of the implant when expanded, and further characterized in that the meandering structures and adjacent meandering structures comprise complementary structures that fit into one another to directly mesh the meandering structures with the adjacent meandering structures in the implant's expanded state and further wherein the meandering structures and adjacent meandering structures are free from direct contact with one another in the implant's compressed state;

wherein the complementary structures are recesses extending from opposing faces of protrusions.

3. The implant according to claim 2, wherein the recesses are at apexes of the protrusions.

* * * * *